United States Patent [19]

Bernat

[11] Patent Number: 4,536,394

[45] Date of Patent: Aug. 20, 1985

[54] ACTIVATED SILICON-CONTAINING ALUMINUM COMPLEX AND PROCESS OF PREPARATION AND USE

[75] Inventor: Fred B. Bernat, Cliffside Park, N.J.

[73] Assignee: San-Mar Laboratories, Inc., Elmsford, N.Y.

[21] Appl. No.: 488,637

[22] Filed: Apr. 26, 1983

[51] Int. Cl.$^3$ .............................................. A61K 33/06
[52] U.S. Cl. .................................................... 424/154
[58] Field of Search ........................ 252/442; 424/154

[56] References Cited

U.S. PATENT DOCUMENTS 4,247,410  1/1981  Bernat .................................. 252/305

*Primary Examiner*—Leonard Schenkman
*Attorney, Agent, or Firm*—Hopgood, Calimafde, Kalil, Blaustein & Judlowe

[57] ABSTRACT

There is disclosed, in one aspect, a process for preparing an activated silicon aluminum complex capable of releasing oxygen and hydrogen in the presence of a halogen compound, such as salt in human perspiration, when added to a fluid which contains oxygen and hydrogen. The process comprises (a) contacting aluminum metal which contains at least trace amounts of silicon with an acid, such as hydrochloric acid, at such concentration that the acid both removes and inhibits formation of oxide on the metal, (b) contacting the thus treated metal with a source of mercury in an oxygen-containing atmosphere such as air, (c) immersing the mercury contacted aluminum in hydrogen halide acid solution at a temperature of from about 5° to about 40° C. for sufficient time to produce a slurry, (d) increasing the pH of the slurry to such an extent that the halogen which is contained in the slurry is neither chemically bound as a halide nor liberated as a halogen gas, (e) adding a source of oxygen gas to the slurry in an amount which depends upon the desired amount of oxygen to be released from the final activated silicon aluminum complex, (f) drying the slurry, (g) at least partially redissolving the solid contained within the slurry in a hydrogen halide, preferably hydrogen chloride, acid solution, (h) cooling the resulting product, and (i) increasing the pH of the cooled product to from about 5.0 to about 5.8. In another aspect, there is disclosed the product formed from this process.

18 Claims, 6 Drawing Figures

ACTIVATED SILICON-CONTAINING ALUMINUM COMPLEX AND PROCESS OF PREPARATION AND USE

BACKGROUND OF THE INVENTION

The present invention relates to a novel silicon-containing aluminum complex and a process for the preparation of that complex. In particular, this complex contains minor amounts of halogen, activated silicon, oxygen and hydrogen in certain proportions such that the complex is capable when added to a hydrogen-and oxygen - containing fluid, of releasing oxygen and hydrogen and enriching the fluid with additional oxygen and hydrogen.

Commercially available non-prescription products which may be applied to the skin, such as cosmetics, beauty aids, antiseptics, medicants, deodorants, etc., work on the basis of either a dilatant or astringent action of the skin pores. Neither way is satisfactory with respect to the cure of acne.

Those compounds which utilize dilatant action may clear the skin of existing impurities but, as a result, the skin pores remain dilated for a considerable period of time, and thus are particularly susceptible to entrance of air polutants such as sulphur dioxide and tar. The result of using such dilatant-action containing products is that, after a short term "success", a worsened skin condition usually occurs.

Those compositions which utilize astringent action are usually applied after the cleaning of the skin with hydrogen peroxide, or other strong oxidizing agents. While the oxygen from the hydrogen peroxide acts effectively and immediately, the subsequent action of the astringent prevents a "deep" cleaning of the skin.

Furthermore, compositions which are used on the skin must help eliminate unpleasant and offensive odors, reduce skin irritations, and dry oxygen lacking impurities on the skin, such as commidones (e.g., blackheads) or acne, depending upon the intended utility of these compositions. Because these compositions are to be used on the skin, they must also be bacteriostatic, non-toxic, non-irritant, and completely safe.

U.S. Pat. No. 4,247,410, filed in the name of the present applicant, discloses an activated silicon-containing aluminum complex containing minor amounts of halogen, silicon, oxygen and hydrogen. The silicon is present in at least trace amounts and has a hexagonal structure. The ratio of oxygen to hydrogen in that complex is usually 16:18. There is also disclosed in this patent a process for preparing that complex.

The complex disclosed in U.S. Pat. No. 4,247,410 is not, however, capable of releasing oxygen and hydrogen over an extended period of time when added to an oxygen and hydrogen-containing fluid.

The search has continued for new and improved compounds useful for releasing hydrogen and oxygen in compositions which may be applied to the skin as well as methods for preparing such compounds. This invention was made as a result of that search.

OBJECTS AND SUMMARY OF THE INVENTION

Accordingly, it is a general object of the present invention to avoid or substantially alleviate the above discussed problems of the prior art.

A more specific object of this invention is to provide an activated silicon aluminum complex which is capable of releasing oxygen and hydrogen in the presence of a halogen containing compound, when added to an oxygen and hydrogen containing fluid.

Another object of this invention is to provide a process for preparing this silicon aluminum complex.

Yet another object of this invention is to provide a process for applying this complex in the form of solid or semi-solid compounds to the skin.

Still another object of this invention is to provide a process for applying this complex in combination with one or more fluids.

Other objects and advantages of this invention will become apparent from the following summary of the invention and description of its preferred embodiment.

The present invention provides, in one aspect, a process for preparing an activated silicon aluminum complex capable of releasing oxygen and hydrogen in the presence of a halogen compound when added to a fluid which contains oxygen and hydrogen. This process comprises:
  (a) contacting aluminum metal which contains at least trace amounts of silicon with a source of an acid of a type and concentration which will both remove and inhibit the formation of oxide on the metal;
  (b) contacting the acid-treated aluminum metal with a source of mercury in an oxygen-containing atmosphere;
  (c) immersing the mercury contacted aluminum in a hydrogen halide acid solution in order to produce a slurry of the mercury contacted aluminum in the acidic solution;
  (d) increasing the pH of the slurry to such an extent that the halogen which is contained in the slurry is neither chemically bound as a halide nor liberated as a halogen gas;
  (e) adding a source of oxygen gas to the slurry in an amount which depends upon the desired amount of oxygen gas to be released from the final activated silicon aluminum complex;
  (f) drying the slurry;
  (g) at least partially redissolving the solid within the slurry in a hydrogen halide acid solution;
  (h) cooling the resulting product; and
  (i) increasing the pH of the cooled product to from about 5.0 to about 5.8.

In another aspect, the present invention provides the product produced by this process.

BRIEF DESCRIPTION OF THE DRAWINGS

For a better understanding of the invention, reference will be made to the accompanying drawings, wherein.

DETAILED DESCRIPTION OF THE PREFERRED EMBODIMENT

The complex of this invention is a light, amorphous, super-oxygenated material, containing aluminum, oxygen, hydrogen and at least trace amounts of unassociated chlorine and silicon. The silicon is in hexagonally structured form. The composition does not burn and it is not explosive.

By the term "activated aluminum" is meant aluminum metal which has been treated with a source of mercury and subsequently formed into a slurry upon prolonged immersion in hydrohalic acid at temperatures of between about ambient and not more than about 40° C. In this "activated" state, the aluminum metal of the slurry remains in its elemental form, but is "clathratic" in that it entraps or confines therein "free" chlorine in trace amounts.

The structure of the trace silicon which is contained in the aluminum metal inherently as an impurity is changed from its normal essentially spherical form to a hexagonal structure. This structural change may be demonstrated by an electromicoscopic examination of the complex in dry form. The change in structure of the silicon is believed to be critical, in order to attain the desired properties of the composition of the present invention. Furthermore, the clathratically entrapped free chlorine enables the present composition to release oxygen and hydrogen.

The activated-silicon containing aluminum complex of this invention may be prepared by a multi-step process. The process will be described in connection with the drawings.

Figure 1:
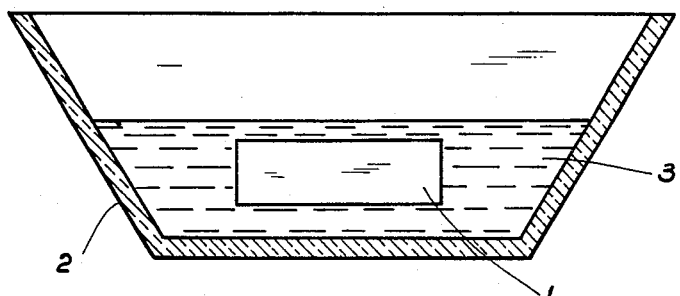
FIG. 1 is a schematic sectional elevational view of an embodiment of the apparatus and ingredients used in the first two steps of the process of the present invention.
Figure 4:
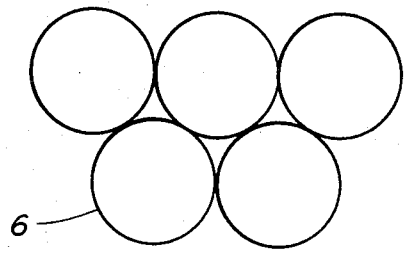
FIG. 4 is a depiction of the structure of untreated, inactive silicon found in untreated aluminum.

Utilizing the apparatus of FIG. 1, an aluminum bar or rod (1) is placed in a vessel (2) which is made preferably of glass or other acid resistant synthetic material. A thin layer of a hydrohalic acid, preferably hydrochloric acid (3), is placed into the vessel such that the aluminum is slightly covered. The shape of the aluminum is not critical, although a bar or rod shape is generally preferred.

The purpose of the acid treatment is to remove any oxide from the aluminum surface, and to inhibit any further development of oxide on the surface. The aluminum should be pure, generally at least about 99.9%, typically at least about 99.94%, and preferably at least about 99.99% pure. The purity of the aluminum may readily be empirically determined since the presence of oxides is demonstrated by an abrupt rise in temperature of the acid solution.

The aluminum metal should not be 100% pure, however. It is necessary that some silicon, generally from about 30 to about 100, typically from about 45 to about 95, and preferably from about 60 to about 90 parts per million (ppm) silicon be present in the aluminum. The use of less than about 30 ppm silicon will lead to a complex which will not contain sufficient hydrogen and oxygen for the desired purpose. The use of more than about 100 ppm silicon will result in process difficulties since silicon tends to heat up the solution and drive off the desired hydrogen and oxygen gases.

Other impurities may be present in the aluminum to the extent discussed above but the amount of iron present in the aluminum should generally be less than about 50, typically less than about 40, and preferably less than about 30% by weight of the silicon. It is desired to keep the iron content to a minimum because iron tends to react with, and thus deplete, the oxygen in the system.

After immersion in the acid solution, the aluminum is then contacted or coated with a source of mercury, preferably by placing such in a bath of the same or similar type of apparatus. This step is carried out in the presence of an oxygen gas-containing atmosphere, such as air. The mercury acts as a catalyst which effects a change in the aluminum structure.

The temperature at which these first two steps are carried out is not critical, but should not be such as to encourage oxide and/or chlorine gas formation. A temperature range of generally from about 10 to about 45, typically from about 15 to about 35, and preferably from about 20° to about 30° C. may be used.

Figure 2:
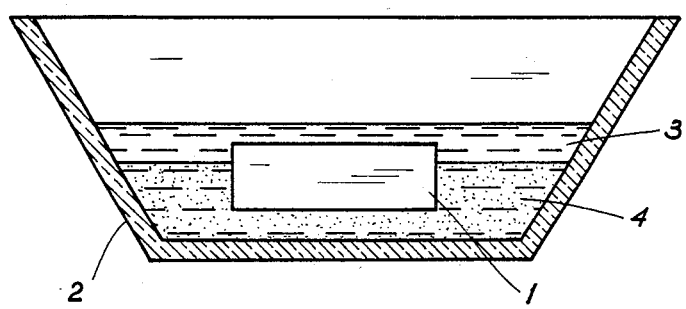
FIG. 2 is a schematic view similar to FIG. 1 showing a different embodiment of the first two steps of the process of the present invention.
Figure 5:
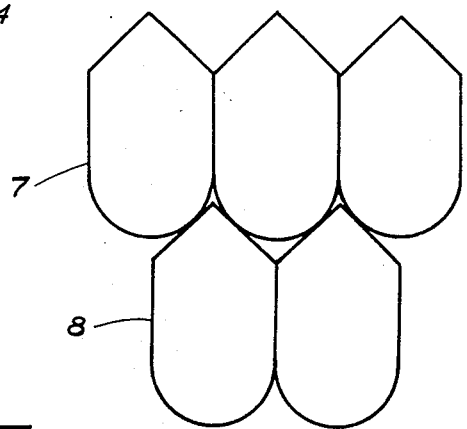
FIG. 5 is a depiction of the hexagonal structure of the silicon of the activated aluminum as contained in the solid powder of the present invention.

If desired, the acid and mercury contact may be made simultaneously as shown in FIG. 2, where aluminum (1) is immersed in acid bath (3) and the heavier mercury bath (4).

Regardless of whether the apparatus of FIGS. 1 or 2 or other suitable apparatus is used, the length of time of contact with the mercury may be relatively short, although longer contact is not detrimental. A time of generally at least about 15, typically from about 15 to about 60, and preferably from about 15 to about 30 seconds may be employed.

The mercury acts as a catalyst which effects a change in the aluminum structure.

The mercury contacted aluminum thus formed is then placed in a hydrogen halide acid solution. A particularly preferred halogen acid for this purpose is hydrochloric acid. This step results in the formation of a slurry of the mercury-contacted aluminum in the acidic solution.

Figure 3:
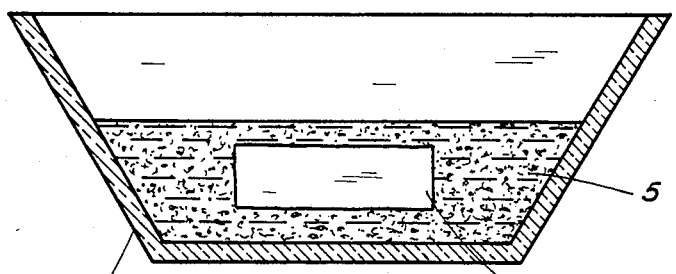
FIG. 3 is a schematic view similar to FIG. 1 showing the formation of a slurry in an hydrochloric acid bath, which takes place during the third step of the process of the present invention.

The slurry may be formed in a number of ways and the method thereof is not critical in and of itself. For example, after contact with mercury, the thus treated aluminum rod or bar may be immersed in another vessel, containing a bath of hydrochloric acid having a concentration which may be empirically determined but which is generally from about 1 to about 2 normal. A rather viscous slurry, white in color, is then formed. The slurry begins as a cloudy suspension and becomes increasingly more dense. This is a consequence of particulate growth in and on the mercury-treated and activated aluminum bar or rod. This growth is shown in FIG. 3 wherein the thick slurry (5) is denoted as forming in the acid bath.

As more and more particles form, the slurry becomes more and more viscous. Depending upon the size of the aluminum bar or the amount of the hydrochloric acid present, the formation of the slurry may continue until all of the aluminum is consumed. As a practical matter, however, the reaction will usually cease prior to the complete consumption of the aluminum since the slurry will become too dense for further growth to occur. At this point, the thick slurry thus formed may be partly or completely removed. Additional hydrochloric acid is then added and slurry formation continues.

The temperature at which this slurry is formed should generally be from about 5 to about 40, typically from about 20° to about 30° C., and preferably from about 22° C. to about 25° C. A sudden adverse rise in temperature of the reaction environment at this point could mean again, that the aluminum starting material was not sufficiently pure. The temperature should not exceed 40° C. because the desired hydrogen and oxygen gases will be released at these higher temperatures. The temperatures should not be less than 5° C. because the reaction rate is not commercially feasible at that temperature.

Alternatively, although less preferably, the slurry may be made in situ in the embodiment set forth in FIG. 2 where the aluminum bar or rod is covered by hydrochloric acid but is also partly submerged in the source of mercury. Optionally, the hydrochloric acid need not continue to cover the aluminum after oxide formation thereon is inhibited. A portion of the aluminum may be exposed above the surface of the hydrochloric acid. In either case, whether the hydrogen chloride continues to cover the surface of the aluminum or not, the complex begins to grow. In either embodiment, the complex is formed by treating oxide-free aluminum with mercury to change the structure of the aluminum and to effect its activation, and then contacting (or continuing to contact) the thus treated aluminum with hydrochloric acid to cause the formation of a slurry.

This slurry has a pH level of from about 3 to about 4. It also contains hydrogen, oxygen, and halogen (preferably chlorine) atoms, probably in ionic form, therein, since this complex has clathrate capabilities, i.e., it can entrap or confine hydrogen, oxygen and chlorine ions within the particles of the slurry.

Next, the pH of the slurry is increased so that the chlorine which is entrapped within the particles of the slurry becomes active. The term "active" as used herein means potentially unstable but not to the extent that the chlorine is liberated as chlorine gas or chloride ion. The pH of the slurry at this point should be generally from about 5.0 to about 5.8, typically from about 5.2 to about 5.6, and preferably from about 5.3 to about 5.5.

This increase in pH may be accomplished by treating the slurry with a strong hydroxide such as sodium hydroxide or potasium hydroxide. The concentration of the hydroxide is not critical and may be generally from about 1 to about 4, typically from about 1.5 to about 3.5, and preferably from about 2 to about 3 normal.

The oxygen content of the slurry is then enriched by adding a source of oxygen, preferably oxygen gas, through a convenient distribution system, such as a pressurized cylinder. Oxygen gas is added until the composition reaches a desired viscosity, generally less than about 18,000, typically less than about 16,000, and preferably from about 12,000 to about 15,000 cps. At this point, the slurry is saturated and does not absorb any additional oxygen gas. The amount of oxygen added determines the amount of oxygen gas to be released from the final activated silicon aluminum complex.

The time necessary for adding oxygen gas may be empirically determined although generally from about 3 to about 10, typically from about 4 to about 8, and preferably from about 5 to about 7 minutes is required.

The oxygenated slurry is then dried either at ambient temperature, or preferably in a convenient drying oven. The heat applied must not be so high that chlorine gas is liberated. The temperature should be generally from about 5 to about 50, typically less than about 40, and preferably from about 20 to about 40° C. The relative humidity should be preferably about 30%.

The length of time needed for drying may be empirically determined since it depends upon the thickness of the layer of slurry and also on the size of the drying oven. Usually drying requires generally from about 30 to about 150, typically from about 50 to about 125, and preferably from about 75 to about 100 minutes. A whitish-grayish powder is the product of this drying step.

Figure 6:
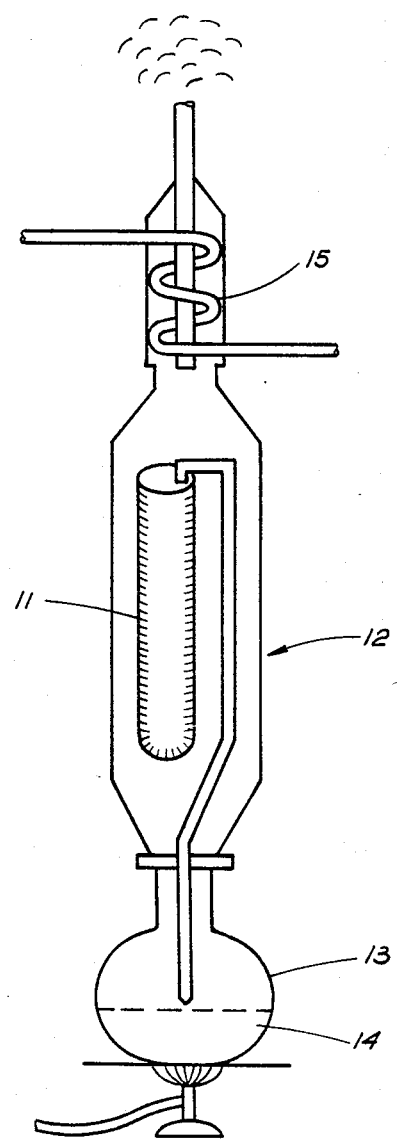
FIG. 6 is a schematic representation of a Soxhlet apparatus in which is carried out the partial redissolution of solid within the slurry.

This powder is then introduced into thimble (11) of a Soxhlet apparatus (12) as shown in FIG. 6. Flask (13) of Soxhlet apparatus (12) is filled with a solution of a hydrohalic acid, preferably hydrochloric acid (14), which is preferably about 3 normal. Flask (13) is then heated by conventional means to the boiling point. The hydrogen chloride vapors penetrate Soxhlet apparatus (12) and, after condensation upon water cooled condenser (15), partially dissolve the powder within thimble (11), and are recirculated within flask (13). This procedure may be repeated until thimble (11) of Soxhlet apparatus (12) is empty.

The amount of time needed to carry out this partial redissolution step may be empirically determined, although generally from about 30 to about 200, typically from about 50 to about 150, and preferably from about 70 to about 120, minutes may be employed. The powder is then recycled in a strong acidic liquid such as hydrochloric acid. It is recycled partly in the form of a solution and partly in the form of a fine cloudy suspension.

After the solution is cooled to a temperature of generally less than about 50, typically from about 15 to about 40, and preferably from about 20° to about 30° C., the pH of the slurry is increased to generally from about 5.0 to about 5.8, typically from about 5.2 to about 5.6 and preferably from about 5.3 to about 5.5.

The pH may be increased by treating it with a strong hydroxide such as sodium hydroxide or potassium hydroxide. The concentration of the hydroxide is not critical and may be generally from about 1 to about 4, typically from about 1.5 to about 3.5, and preferably from about 3 to about 4 normal.

This increase in pH may be monitored with a conventional pH meter.

This increased pH slurry comprises the complex of this invention. It may be used in various formulae in the field of cosmetics, beauty aids, medicants, deodorants, etc., in various percentages which may readily be determined empirically.

This complex, even in small amounts, has the unique ability of releasing oxygen and hydrogen when introduced in an oxygen and hydrogen-containing composition, such as cosmetics, medicants, beauty aids, deodorants, etc. It is critical, however, for the release of oxygen and hydrogen, that a halogen salt, such as sodium chloride, be present as a catalyst.

The complex may be used in the following percentages by weight of the total composition depending upon end use: acne (about 3%), depilatory (about 4.5 to 5%), face cream (about 5%), underarm deodorant (about 3%).

The present invention is further illustrated by the following examples. All parts and percentages in the examples as well as in the specification and claims are by weight unless otherwise specified.

EXAMPLE 1

Five hundred grams of aluminum metal rod, having not more than 0.02% of impurities is placed in a 36 inch long shallow glass vessel as shown by FIG. 1. The aluminum is contacted with 3N hydrochloric acid at 20° C. in amounts sufficient to cover the aluminum rod. Thereafter the aluminum rod is removed from the acid bath and immersed in a mercury bath for approximately 10 minutes under moist (relative humidity of about 30%) air-atmospheric conditions.

The mercury contacted aluminum rod is then reimmersed in a bath of 2N hydrochloric acid. A growth is observed on all sides of the immersed surface of aluminum and the aluminum bar begins to dissolve in the hydrochloric acid bath.

Almost immediately a milky white cloud begins to appear. After about 8 hours a slurry may be discerned within the acid bath. The temperature is kept below 30° C. The reaction is allowed to continue until all of the aluminum bar is consumed. Before the bar is consumed, however, the slurry becomes so thick the reaction is severely inhibited. This occurs after about 48 hours. This thick slurry is then removed and fresh hydrochloric acid added. This process is continued until the aluminum is completely dissolved. The slurry thus produced has a pH of 3.54 which is then increased to 5.4 by the addition of sufficient 2N sodium hydroxide.

A stream of oxygen gas is slowly passed through the slurry. The flow is monitored with a Beckman analyzer, until it is determined that it has acquired an additional two atoms of oxygen i.e., that the number of oxygen atoms increased from 16 to 18. The viscosity of this slurry is about 15,000 cps.

The slurry is then spread upon a thin layer over a plastic tray and placed in a commercially available drying oven. The oven is heated to a temperature of about 40° C. while under substantially anhydrous conditions, i.e., a humidity of about 19%. After about an hour, the slurry is dried to a whitish-grayish powder and removed from the drying oven.

Two hundred grams of this powder is then introduced into thimble (11) of Soxhlet apparatus (12). Flask (13) is filled with 1000 milliliters of 3N hydrochloric acid (14) and heated to the boiling point. The hydrochloric acid continues to boil and the acidic liquid is recycled four times during a period of about 90 minutes. At that point, thimble (11) of Soxhlet apparatus (12) is empty, and the liquid in flask (13) of the Soxhlet apparatus contains a fine cloudy suspension. After the solution is cooled to about 200° C., a 3N potassium hydroxide solution is slowly added, until the pH increases to about 5.4. This pH increase is monitored with a Beckman pH-meter. At that point the product may be used in specific cosmetic, deodorant, medicant and other formulations.

EXAMPLE 2

This example illustrates the application of the complex of this invention in the field of health and beauty-aids, particularly the preparation of an acne-removing formulation:

The following ingredients set forth in the following TABLE are mixed together in a Waring blender until a homogeneous composition is obtained.

TABLE

| Ingredient | Percentage* |
| --- | --- |
| Deionized water | 65.419 |
| Activated Silicon-Aluminum Complex | 3.000 |
| Sodium Dodecylbenzene Sulfonate | 1.800 |
| Potassium Xylene Sulfonate | 3.550 |
| Citric Acid (Anhydrous USP) | 0.366 |
| Antifoam AF | 0.005 |
| Salicylic Acid | 0.500 |
| Alpine Perfume 6321 | 0.050 |
| Ethyl Alcohol 95% | 23.000 |
| Sodium Carbonate (Anhydrous) | 0.060 |
| Supercel (filter aid) | 0.250 |
| Triethanolamine | 2.000 |

TABLE-continued

| Ingredient | Percentage* |
| --- | --- |
| | 100.000% |

*By Weight Of Total Composition

This composition may be applied directly to skin containing acne lesions.

The complex of this invention works in a manner substantially different from that of prior art compositions. While it is slightly astringent, the present complex neither closes nor dilates the pores. Since it is rich in readily liberated oxygen and since it is activated by halogen salts such as sodium chloride (present in perspiration from the surface of the skin), this complex releases a constant and steady flow of oxygen.

Commidones (blackheads) are immediately attacked by this released oxygen. Since commidones are isolated, foreign materials, which have no oxygen supply like the rest of the skin, they become "oxygen-hungry". The oxygen from the complex penetrates the commidones readily and efficiently and dries them out, while the rest of the skin is unaffected. By using an oxygen carrier-compound such as described above in the acne-removing formula, the affected skin is under control during the period of development of the acne.

This complex may be used in other compositions which are used on the skin. One such composition is an underarm deodorant. Problems are encountered with prior art underarm deodorants in applying the correct amount to the underarm area. Too little will not be effective. Too much might irritate. The present complex, however, is non-irritating to the skin. Furthermore, the salt in perspiration triggers the release of hydrogen and oxygen. When the perspiration stops, the action of the complex also stops. When perspiration re-commences, the action of the complex also re-commences.

While the scientific phenomena upon which this invention is based is not fully understood, and I do not wish to be bound by any particular theory, it is believed that the subgrain structure of aluminum appears to undergo profound changes when under chemical and electrochemical attack.

The spheroidal shape of the silicon trace material in aluminum changes to the hexagonal shape as a result of the "free chlorine" of the slurry, and due to the interaction of the mercury-treated aluminum with the hydrochloric acid solution. This change in structure which may be observed in the oxygenated solid powder of this invention is also believed to be related to the phenomenon which enables the complex of this invention to release oxygen and hydrogen in presence of a catalyst.

Furthermore, when ordinary aluminum is introduced into an hydrochloric acid solution, e.g., 1N or 2N, the production of aluminum chloride (and water) takes place. However, when the mercury treated aluminum which is used in the process of this invention is placed in hydrochloric acid the behavior is quite different. While there still results the formation of aluminum chloride as well as other aluminum compounds, after the passage of from about 8 to about 72 hours a slurry, which begins as a faint white cloud, is formed. This slurry is a result of a growth on the treated aluminum. The growth then falls or flakes off into the acid bath and begins to form the slurry. After about 8 hours or so, the slurry is in full "bloom" and a discernible increase in viscosity begins to occur, leading to the preferred viscosity range of from about 13,000 to about 15,000 cps.

In this slurry, a relatively small amount, perhaps from about 0.7 to about 1.5% by weight, of "activated" aluminum particles is suspended, perhaps as a colloid. These particles, however, contain entrapped therein because of their clathrate properties "free chlorine" (from the hydrochloric acid), oxygen, and hydrogen probably in molecular or ionic form. The silicon of the aluminum has also been changed to the hexagonal structure.

Thus the slurry contains both the reaction product of aluminum and hydrochloric acid in solution, e.g., aluminum, chloride, hydrogen, and hydroxide ions, and free "activated" aluminum suspended, probably colloidally. The aluminum contains hexagonally structured silicon as well as hydrogen and oxygen entrapped therein.

The unusual properties of this slurry may possibly also be explainable in terms of "Van der Waal's forces" or the well-known ability of particles in colloidal suspension to attract and retain on their surface dissolved substances and solvent molecules, i.e., to have molecules present in the solution even in ionic form become entrapped in or to adhere to the particulate matter of the slurry or colloid.

When the slurry is oxygenated, it acquires additional oxygen, again probably due to the clathratic properties of the suspended activated aluminum particles, and/or the action of the Van der Waal forces or solid colloidal attractions as discussed above. At this point, the slurry has become what I call "super-oxygenated".

When this dried "super-oxygenated" slurry is treated in the Soxhlet apparatus with hydrogen chloride and the pH is raised to about 5.4, the same slurry is now in liquid form with its viscosity reduced to between about 1.1 and 1.2. It is now capable of withholding the release of oxygen and hydrogen except in the presence of a halogen salt, such as sodium chloride, which is present in perspiration. The presence of the halogen salt triggers the slow and steady release of oxygen and hydrogen, until the halogen salt is completely consumed.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

I claim:

1. A process for preparing a suspension of an activated silicon aluminum complex which is capable of releasing oxygen and hydrogen in the presence of a halogen compound, said process comprising:
   (a) contacting aluminum metal having a purity of at least about 99.9% by weight and containing at least trace amounts of silicon, with a source of an acid of a type and concentration which will both remove and inhibit the formation of oxide on said metal;
   (b) contacting said acid-treated aluminum metal with a source of mercury in an oxygen-containing atmosphere;
   (c) partially immersing said mercury contacted aluminum in a hydrogen halide solution for sufficient time to begin the growth of a complex on said mercry-contacted aluminum;
   (d) treating said complex with acid to increase the pH to such an extent that the halogen which is contained in said complex is neither chemically bound as a halide nor liberated as a halogen gas;
   (e) adding a source of oxygen gas to said acid treated complex solution in an amount which depends upon the desired amount of oxygen gas to be released from the final activated silicon aluminum complex;
   (f) drying said oxygenated and acid treated complex;
   (g) at least partially redissolving said complex in a hydrogen halide acid solution to form a suspension;
   (h) cooling said suspension; and
   (i) increasing the pH of said suspension to from about 5.0 to about 5.8.

2. The product of the process of claim 1.

3. The process of claim 1 wherein said aluminum is at least about 99.94% pure and contains from about 60 to about 90 ppm silicon and less than about 40% by weight iron based upon the weight of said silicon.

4. The process of claim 1 wherein step (c) is carried out at a temperature of from about 5° to about 40° C.

5. The process of claim 1 wherein the pH is increased in step (d) to from about 5.2 to about 5.6.

6. The process of claim 1 wherein the source of oxygen gas in step (e) is substantially pure oxygen gas and sufficient oxygen gas is added to raise the viscosity of said acid treated complex solution to less than about 16,000 cps.

7. The process of claim 1 wherein said oxygenated and acid treated complex is dried at a temperature of from about 5° to about 50° C.

8. The product of the process of claim 3.

9. The product of the process of claim 4.

10. The product of the process of claim 5.

11. The product of the process of claim 6.

12. The product of the process of claim 7.

13. The process of claim 1 wherein said hydrogen halide acid is hydrochloric acid.

14. The product of the process of claim 13.

15. A process for preparing a suspension of an activated silicon aluminum complex which is capable of releasing oxygen and hydrogen in the presence of a halogen compound, said process comprising:
   (a) contacting aluminum metal having a purity of at least 99.99% by weight, and containing from about 60 to about 99 ppm silicon and less than about 30% by weight iron based on the weight of said silicon, with hydrochloric acid of a concentration which will both remove and inhibit the formation of oxide on said metal;
   (b) contacting said acid-treated aluminum metal with mercury metal in an oxygen-containing atmosphere;
   (c) partially immersing said mercury contacted aluminum in a hydrogen chloride solution at a temperature of from about 20° to about 30° C. for sufficient time to begin the growth of a complex on said mercury-contacted aluminum;
   (d) treating said complex with acid to increase the pH to from about 5.3 to about 5.5;
   (e) adding oxygen gas to said acid treated complex solution in such an amount that the viscosity of said solution increases to from about 12,000 to about 15,000 cps.
   (f) drying said oxygenated and acid treated complex at a temperature of from about 20° to about 40° C.;

(g) at least partially redissolving said complex in a hydrogen chloride acid solution to form a suspension;

(h) cooling said suspension to a temperature less than about 50° C.; and (i) increasing the pH of said suspension to from about 5.3 to about 5.5.

16. The product of the process of claim 15.

17. A process for releasing oxygen to the skin comprising applying to the skin an amount of the complex of claim 2 to supply a steady flow of oxygen to the skin.

18. A process for releasing oxygen to the skin comprising applying to the skin an amount of the complex of claim 16 to supply a steady flow of oxygen to the skin.

* * * * *